(12) United States Patent
Connor et al.

(10) Patent No.: US 6,929,922 B1
(45) Date of Patent: Aug. 16, 2005

(54) METHODS FOR THE DETECTION OF DEMYELINATING DISEASES

(75) Inventors: James R. Connor, Hershey, PA (US); Stanley W. Hulet, Joppa, MD (US)

(73) Assignee: The Penn State Research Foundation, University Park, PA (US)

( * ) Notice: Subject to any disclaimer, the term of this patent is extended or adjusted under 35 U.S.C. 154(b) by 0 days.

(21) Appl. No.: 09/500,713

(22) Filed: Feb. 9, 2000

Related U.S. Application Data
(60) Provisional application No. 60/119,359, filed on Feb. 9, 1999.

(51) Int. Cl.[7] ...................... G01N 33/53; G01N 33/567; G01N 33/566
(52) U.S. Cl. ...................... 435/7.2; 435/7.21; 436/501; 436/503; 436/504
(58) Field of Search ................................. 435/7.2, 7.21, 435/72, 7; 436/501, 503, 504, 16; 424/9; 600/12; 530/350

(56) References Cited

U.S. PATENT DOCUMENTS

| | | | | |
|---|---|---|---|---|
| 4,737,456 A | * | 4/1988 | Weng et al. | .................... 435/7 |
| 4,813,399 A | * | 3/1989 | Gordon | ........................ 600/12 |

OTHER PUBLICATIONS

Harrison's Principles of Internal Medicine, p. 1995–2000 (11th ed. 1987).
Bourdette, DN, et al., "Health Care Costs Of Veterans With Multiple Sclerosis: Implications For The Rehabilitation of MS.," Arch Phys Med Rehabil, 74, pp. 26–31, 1993.
Wucherpfenning KW, Strominger JL. "Molecular Mimicry in T Cell Mediated Autoimmunity: Viral Peptides Activate Human T Cell Clones Specific for Myelin Basic Protein," Cell 80: 695–705, 1995.
Martin R, et al., "Immunological Aspects of Demyelinating Disease," Annu Rev Immunol 10:153–87, 1992.
Hafler DA, Weiner HL. "Immunologic Mechanisms and Therapy in Multiple Sclerosis." Immunol Rev 144:75–107, 1995.
Hohfeld R, et al. "The Role of Autoimmune T Lymphocytes in the Pathogenesis of Multiple Sclerosis," Neurology 45 (6 Suppl 6):S33–8, 1995.
Steinman L, "A Few Autoreactive Cells in an Autoimmune Infiltrate Control a Vast Population of Nonspecific Cells: a Tale of Smart Bombs and the Infantry," Proc Natl Acad Sci USA 93: 2253–6, 1996.
Hafler DA, et al., "TCR Usage in Human and Experimental Demyelinating Disease," Immunol Today 1996; 17: 152–9, 1996.
Padovan E, et al., "Expression of Two T Cell Receptor α Chains: Dual Receptor T Cells," Science 262:422–4, 1993.

Davodeau F, et al. "Dual T Cell Receptor β Chain Expression on Human T Lymphocytes," J. Exp Med 181: 1391–8, 1995.
Padovan E, et al., "Normal T Lymphocytes Can Express Two Different T Cell Receptor β Chains: Implications for the Mechansim of Allelic Exclusion" J Exp Med 181: 1587–91, 1995.
Marrack P. et al., The Staphylococcal Enterotoxins and Their Relatives [published erratum appears in Science 1990: 248 1066] Science 248: 705–11, 1990.
Hoffman, M., ""Superantigens" May Shed Light on Immune Puzzle," Science 248:685–6, 1990.
Kotzin BL, et al., "Superantigens and Their Potential Role in Human Disease," Adv. Immunol 54:99–166, 1993.
Scherer MT, et al., "Superantigens: Bacterial and Viral Proteins That Manipulate the Immune System," Annu Rev Cell Biol 9:101–28, 1993.
Brocke S, et al., "Infection and Multipple Sclerosis: A Possible Role for Superantigens?," Trends Microbiol 2:250–4, 1994.
Thorpe JW, et al., "Serial Gadolinium–enhanced MRI of the Brain and Spinal Cord in Early Relapsing–Remitting Multiple Sclerosis," Neurology 46:378–8, 1996.
Wekerle H, et al., "Cellular Immune Reactivity Within the CNS," Trends Neurosci 9:271–7, 1986.
Butcher EC, Picker LJ., "Lymphocyte Homing and Homeostasis," Science 272:60–6, 1996.
Shrikant P, Benveniste EN, "The Central Nervous System as an Immunocompetent Organ. Role of Glial Cells in Antigen Presentation," J Immunol 157:1819–22, 1996.
Vass K, Lassmann H., "Intrathecal Application of Interferon Gamma. Progressive Apperance of MHC Antigens within the Rat Nervous System," Am J Pathol 137: 789–800, 1990.
Lassmann H, Rossler K, Zimprich F, Vass K., "Expression of Adhesion Molecules and Histocompatibility Antigens at the Blood–Brain Barrier," Brain Pathol 1:115–23, 1991.
Lassmann H., et al. , "Microglial Cells are a Component of the Perivascular Glia Limitans," J Neurosci Res. 28: 236–43, 1991.
Fabry Z, Raine CS, Hart MN, "Nervous Tissue as an Immune Compartment: the Dialect of the Immune Response in the CNS," Immunol Today 15:218–24, 1994.
Fontana A, Fierz W, Werkle H, "Astrocytes Present Myelin Basic Protein to Encephalitogenic T Cell Lines," Nature 307:273–6, 1984.

(Continued)

Primary Examiner—Olga N. Chernyshev
(74) Attorney, Agent, or Firm—Medlen & Carroll, LLP

(57) ABSTRACT

Methods are described for the use of transferrin binding as the basis for a diagnostic assay to identify pathologies consistent with demyelinating diseases including Multiple Sclerosis. In a specific embodiment the evaluation of transferrin binding, in brain tissue, is used in a method for the detection of multiple sclerosis.

1 Claim, 9 Drawing Sheets

OTHER PUBLICATIONS

Weber F, et al., "Human Astrocytes are only Partially Component Antigen Presenting Cells: Possible Implications for Lesion Development in Multiple Sclerosis," *Brain* 117: 59–69, 1994.

Meinl E, et al., "Multiple Sclerosis: Immunomodulatory Effects of Human Astrocytes on T Cells," *Brain* 117:1323–32, 1994.

Kojima K, et al., "Experimental Autoimmune Panencephalitis and Uveoretinitis Transferred to the Lewis Rat by T Lymphocytes Specific for the S100β Molecule, a Calcium Binding Protein of Astroglia," *J Exp Med* 180:817–29, 1994.

Linington C, et al., "Augmentation of Demyelination in Rat Acute Allergic Encephalomyelitis by Circulating Mouse Monoclonal Antibodies Directed Against a Myelin/Oligodendrocyte Glycoprotein," *Am J. Pathol* 130:443–54, 1988.

Genain CP, et al., "Antibody Facilitation of Multiple Sclerosis–Like Lesions in a Nonhuman Primate," *J Clin Invest* 96: 2966–74, 1995a.

Linington C, et al., "T Cells Specific for the Myelin Oligodendrocyte Glycoprotein Mediate and Unusual Autoimmune Inflammatory Response in the Central Nervous System," *Euro J immunol* 23:1364–72, 1993.

Ozawa K, et al., "Petterns of Oligodendroglia Pathology in Multiple Sclerosis," *Brain* 117:1311–22, 1994.

Hohlfeld, R., "Biotechnological Agents For The Immunotherapy Of Multiple Sclerosis," *Brain*, 120, pp. 865–916, 1997.

Douillard and Hoffman, "Basic Facts about Hybridomas," in *Compendium of Immunology* vol. II, ed. by Schwartz, pp. 119–141, 1981.

Kohler and Milstein, "Continous cultures of fused cells secreting antibody of predifined specificity," *Nature* 256: 495–499, 1975.

Kohler, G. et al., "Derivation of specific antibody–producing tissue culture and tumor lines by cell fusion," *European Journal of Immunology* 6: 511–519, 1976.

* cited by examiner $I^{125}$ Recombinant Ferritin Overlay on Oligodendrocytes

METHODS FOR THE DETECTION OF DEMYELINATING DISEASES

RELATED U.S. APPLICATION DATA

This application claims priority to copending application U.S. Provisional Patent Application Ser. No. 60/119,359 filed on Feb. 9, 1999.

STATEMENT OF GOVERNMENTAL INTEREST

This invention was made with government support awarded by the National Institutes of Health under grant numbers NS 22671 and NS 34280. The Government has certain rights in the invention.

FIELD OF THE INVENTION

The present invention relates to methods for detecting demyelinating diseases including Multiple Sclerosis (MS). Specifically, changes in ferritin binding in the brain and the detection of antibodies against ferritin binding protein are used as indices to confirm the presence of degenerative demyelinated lesions in the brain that, in one example, are consistent with the histopathology of MS.

BACKGROUND

Multiple sclerosis ("MS") is a disease which presents as recurrent attacks of focal or multifocal neurologic dysfunction. Its symptoms are multi-faceted and indefinite and include (but are not limited to) impaired vision, nystagmus, an inability to speak clearly, a decreased perception of vibration and position sense, intention tremor, muscular incoordination, limb weakness or paralysis, spasticity, and bladder problems. Harrison's Principles of Internal Medicine, p. 1995–2000 (11th ed. 1987).

The economic sequelae of MS are substantial. A cost of illness (COI) study conducted by Bourdette et al. retrospectively examined costs to the US Veterans Affairs (VA) for the treatment of 165 patients with MS over a 3-year period. Bourdette, D N, et al. Health Care Costs Of Veterans With Multiple Sclerosis: Implications For The Rehabilitation of MS. Arch Phys Med Rehabil, 74, pp. 26–31 (1993). Drug costs were not included in the study. The average cost to the VA associated with these patients was estimated at $35,000 per year.

Homes et al. conducted a prevalence-based COI study, surveying 672 members of the Multiple Sclerosis Society in the UK. Holmes, B A, et al. Br. J. Med Econ, 8, pp. 181–93. (1995). This study reported an annual burden, associated with medical cost and lost wages from MS, estimated at £1.2 billion for 1994. The state carried the largest burden with the principal cost drivers being state benefits (23.9% of total costs). National Health Service costs (12.8%) and lost tax revenue (12.3%). Drug costs were assumed to be nonsignificant and, therefore, were not included in the study. The burden of caring for patients with MS fell more heavily on hospitals and nursing homes, over general practitioners (GPs). The burden on the individual approximated that on the state, with 33% of total costs resulting from lost earnings (including caregiver and patient), and 11.7% attributable to private expenses. The remaining 6.3% of the total burden was borne by industry.

In order to establish a definite diagnosis of MS, accepted practice mandates that at least two episodes of neurological deficit must occur along with objective clinical signs of lesions at more than one site within the central nervous system. One problem with such a diagnostic method is that a period of ten to twenty years may pass between episodes of neurological deficit.

Another problem is that the symptoms of MS are so indefinite that it may be confused with several other conditions. It is therefore important during the differential diagnosis of the patient to exclude conditions having similar symptoms which can be effectively treated. For example a patient may be suffering from side-effects of various prescription drugs (e.g. phenytoin which can cause nystagmus, vertigo and muscle weakness), pernicious anemia, or various infections. Usually such conditions can be effectively treated. Therefore, a need exists for diagnostic methods for the early detection of pathological processes consistent with a diagnosis of demyelinating disease including, in one example, MS.

SUMMARY OF THE INVENTION

The present invention contemplates using both histological and immunological assays for the early detection of pathologies consistent with demyelinating diseases including MS. The invention is based on the distribution of ferritin receptors in the brain and the pathological production of antibodies against these receptors in persons afflicted with MS.

In one embodiment, the present invention contemplates evaluation of biopsies brains tissue, by histological methods, to detect changes consistent with the degenerative processes of MS. In another embodiment, the invention contemplates the detection of antibodies (e.g. in the serum) against ferritin binding protein in the brain as a marker for MS consistent with autoimmulogical activity observed in persons afflicted with MS.

In one embodiment, the present invention provides a method for the detection of a demyelinating disease comprising providing, i) a sample from a human suspected of having a demyelinating disease and ii) iron binding protein, reacting said sample with said iron binding protein, and measuring the extent of binding of said iron binding protein to said sample.

In one embodiment, the sample from a human suspected of having a demyelinating disease is brain tissue. The brain tissue is conveniently collected via surgical biopsy.

In another embodiment, the iron binding protein is ferritin isolated from native or recombinant sources. Notwithstanding of the ferritin source, ferritin may be linked to a detectable marker. Such a detectable marker is selected from the group consisting of radioisotope, in one example $^{125}$I, and florescent dye.

In another embodiment, measuring the extent of binding of said iron binding protein to said sample is performed with a technique selected from the group of autoradiography and immunofluorescence.

The present invention also contemplates a method for the detection of a demyelinating disease comprising providing a fluid sample from a human suspected of having a demyelinating disease, reacting said fluid sample with human ferritin binding protein, and detecting the binding of antibodies within said fluid sample to said ferritin binding protein.

In one embodiment, the fluid sample is selected from the group consisting of whole blood, blood serum, blood plasma, cerebral spinal fluid, lymph, and urine.

In another embodiment, the ferritin binding protein is immobilized prior to reacting said fluid sample with human ferritin binding protein.

In another embodiment, the ferritin binding protein is immobilized on a substrate selected from the group consisting of glass, agarose, and plastic.

In another embodiment, the ferritin binding protein is operably linked with a resin.

The present invention also contemplates an isolated ferritin binding protein having an observed molecular weight of approximately 55 kDa.

The present invention is not limited in the types of uses or embodiments that are contemplated. While a variety of applications for the methods and products herein described are contemplated, the applications are not limited.

DESCRIPTION OF THE DRAWINGS

To facilitate an understanding of the invention, a number of Figures are included herein.

DEFINITIONS

Figure 1:
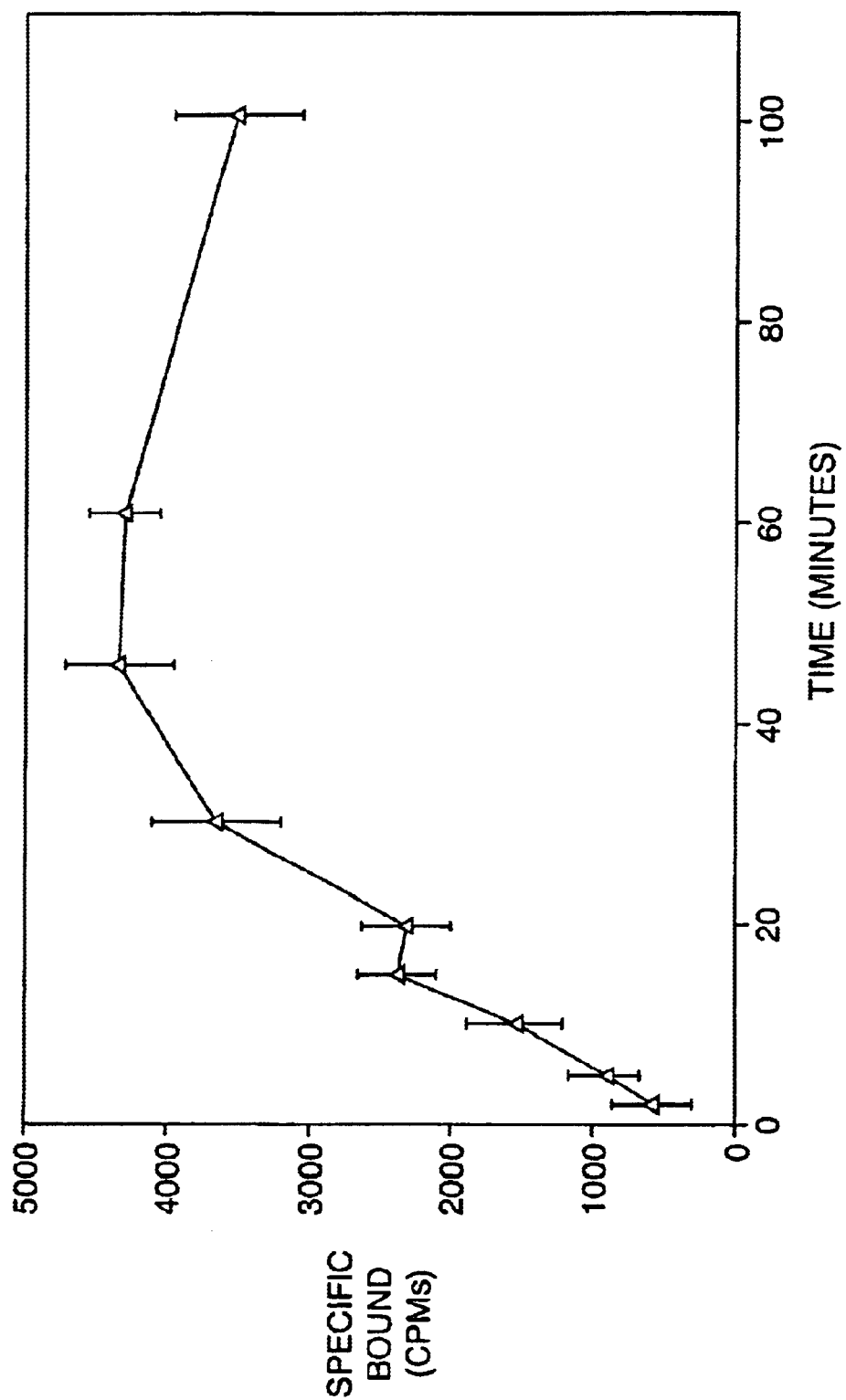
FIG. 1 presents a time course analysis of specific rH-ferritin binding to isolated human membranes. $^{125}$I rH-ferritin (0.2 nM) was incubated with 25 μgs of membrane homogenate at 22° C. for up to 100 minutes. Each point of the curve represents the mean of analyses from 3 different human preparations each performed in duplicate ±SEM. Steady state of binding is reached after 45 minutes.

To facilitate an understanding of the invention, a number of terms are defined.

As used herein, the term "demyelinating disease" refers to any pathological process that results in the degradation or loss of the myelin sheath surrounding an axon including, but not limited to, Multiple Sclerosis and Guillain-Barre syndrome.

As used herein, the term "Multiple Sclerosis" refers to a demyelinating disorder of the central nervous system characterized, anatomically, by sclerotic plaques in the brain and spinal cord producing symptoms including (but not limited to) visual loss, diplopia, nystagmus, dysarthria, weakness, paresthesias, and bladder abnormalities.

As used herein, the term "fluid sample" refers to samples taken from whole blood, blood plasma, blood serum, extravascular fluid, cerebral spinal fluid, lymph, interstitial fluid, pleural fluid, prostatic fluid, sucular fluid, ventricular fluid, synovial fluid, and stool.

As used herein, the term "tissue" refers to a collection of similar cells and the intercellualr substances around said cells.

As used herein, the term "white matter" refers to those regions of the brain and spinal cord that are substantially composed of nerve fibers and contain few neuronal cell bodies or dendrites.

As used herein, the term "grey matter" refers to those regions of the brain and spinal cord that are made up substantially of the cell bodies and dendrites of nerve cells rather than myelinated axons.

DESCRIPTION OF THE INVENTION

The present invention contemplates using both histological and immunological assays for the early detection of pathologies consistent with demyelinating diseases including MS. The invention is based on the distribution of ferritin receptors in the brain and the pathological production of antibodies against these receptors in persons afflicted with MS.

The Role of Iron in Myelination

Iron is a key element in the multi-factorial initiation of myelination. Furthermore, it is well established that the principle cells which stain for iron within the brain are oligodendrocytes, the cells which produce myelin. Iron positive cells are abundant in all white matter tracts consistent with reports that iron levels in white matter are higher than in gray. Iron uptake into the brain is maximal during rapid brain growth which coincides with the peak of myelinogenesis. Iron is required for galactocerebroside expression by oligodendrocytes in culture as well as for cholesterol and lipid biosynthesis which are key components of myelin. Iron deficiency is associated with hypomyelination. Conversely, intracerebral injection of the iron transport protein transferrin into young rats induced approximately a 40% increase in myelin total proteins. Clearly, iron is a vital component for the onset of myelination, but its continuous requirement for myelin maintenance is less clear because of the lack of evidence for transferrin receptor expression on adult oligodendrocytes.

Transferrin receptors are expressed by oligodendrocytes during their initial stages of development both in vivo and in vitro. The appearance of transferrin receptor-positive cells, both in vivo and in vitro, precedes the expression of transferrin, myelin basic protein and galactocerebroside. However, the expression of transferrin receptors by oligodendrocytes decreases in density with age. Autoradiographic evidence shows that transferrin receptors are distributed primarily throughout gray matter areas of the human and adult rat brain but not in the iron rich white matter tracts. These same autoradiographic data, however, confirm that ferritin binds to the white matter of the brain and that this binding decreases in and around demylentating lesions associated with MS.

Ferritin Distribution in the Human Brain

Ferritin comprises 24 subunits of H (heavy) or L (light) chain peptides that exist in varying ratios. The ratio of H/L subunits at the protein level is organ specific. For example, the liver contains ferritin predominantly made of L subunits, whereas the heart contains predominantly H-ferritin. The H subunit contains ferroxidase activity and is responsible for converting soluble ferrous ($Fe^{+2}$) iron to the storable ferric form. The L subunit does not have ferroxidase activity and thus stores iron at a very low rate compared with the H subunit. The proposed function of the L subunit is to promote mineralization of iron at the ferritin core, whereas rapid uptake and reutilization of iron is more associated with H-rich ferritin. Applicants have measured the H/L ratio in adult human brain ferritin and found that H-ferritin is on average 2x more abundant than L (data not shown).

Distribution of Ferritin in Brain Tissue as a Diagnostic for MS

In one embodiment of the present invention, the binding of ferritin to white matter (e.g. myelinated nervous tissue) is used as a diagnostic to identify pathological cerebral lesion consistent with MS.

The principle cells that stain for iron within the brain are oligodendrocytes, the cells which produce myelin. However the distribution of the receptor for the iron transport protein transferrin is primarily throughout grey matter. To date, these data (which suggest a dynamic requirement for iron in maintaining myelin production) could not be reconciled with the apparent lack of an iron delivery protein in adult white matter.

Applicants demonstrate the distribution of ferritin binding is opposite of that seen for the distribution of the transferrin receptor in normal adult human brain (predominantly found in gray matter). Applicants demonstrate the normal distributions of transferrin and ferritin binding sites are altered in and around plaques from periventricular white matter isolated from multiple sclerotic (MS) brains. In direct contrast to ferritin binding, transferrin binding in the MS tissue can be seen in white matter periplaque regions and to varying degrees within the lesion itself. The transferrin binding in the periplaque region is to oligodendrocytes as indicated by immunocytochemistry for the transferrin receptor.

However, the loss of ferritin binding in the periplaque regions indicates the immature oligodendrocytes are attempting to re-myelinate but never mature to the point of expressing ferritin receptors. Furthermore, ferritin binding is absent within the lesion itself which suggests ferritin is not binding to microglia or astrocytes; the two other types of glial cells found in white matter and which heavily populate the lesion. Furthermore, Applicants show the distribution of ferritin and transferrin binding sites in human brain is non-overlapping and that immature oligodendrocytes bind transferrin whereas the mature, myelinating oligodendrocytes bind ferritin. These data prove that iron acquisition during oligodendrocyte maturation is under specific temporal regulation and determine whether the cells develop fully to support and maintain myelination.

Therefore the present invention contemplates assay systems which are based on the differential binding of ferritin in normal brains and the brains of persons afflicted with MS. In a preferred embodiment, immunocytochemical methods are used identify demyelinated lesions in the brain (consistent with a finding of MS) which substantially fail to bind ferritin.

Immunopathogenesis of Multiple Sclerosis

Potentially autoaggressive T lymphocytes specific for myelin basic protein (MBP) or other autoantigens of the central nervous system pre-exist in the normal immune system of rodents and primates. These autoreactive T cells likely escaped from the thymic control mechanism of clonal deletion.

While the pathogenesis of MS is poorly understood it is likely the disease is initiated by anergic, suppressed or ignorant T cells in the "periphery" outside the central nervous system (CNS). Experimental models illuminate various scenarios that may contribute to the progression of MS. However, it is not intended that the present invention be limited by the mechanism presented in any of these models. Instead, these models are offered as a foundation to substantiate the basis for diagnostic methods for the detection of MS based on the detection of pathologic immune responses.

In one scenario the initial activation of autoreactive T cells occurs via "molecular mimicry" during bacterial or viral infection. Many bacterial and viral proteins share short sequence homologies with autoantigens. It is important to note that contiguous identity is not required: even seemingly unrelated amino acid sequences may, together with "presenting" major histocompatibility complex (MHC) molecule, assume a structure that allows them to cross-stimulate autoantigen-specific T cells. MBP serves as a good example to illustrate this point. One of the sequences preferentially recognized by human MBP-specific T cells is region MBP of the MBP molecule (Wucherpfenning K W, Strominger J L. *Molecular Mimicry in T Cell Mediated Autoimmunity: Viral Peptides Activate Human T Cell Clones Specific for Myelin Basic Protein.* Cell 1995; 80: 695–705: Martin R, McFarland H F, McFarlin D E. *Immunological Aspects of Demyelinating Disease.* [Review]. Annu Rev Immunol 1992; 10:153–87; Hafler D A, Weiner H L. *Immunologic Mechanisms and Therapy in Multiple Sclerosis.* [Review]. Immunol Rev 1995; 144:75–07; Hohfeld R, Meinl E, Weber F, Zipp F, Schmidt S, Sotgiu S, et al. *The Role of Autoimmune T Lymphocytes in the Pathogenesis of Multiple Sclerosis.* [Review]. Neurology 1995; 45 (6 Suppl 6):S33–8: Steinman L, *A Few Autoreactive Cells in an Autoimmune Infiltrate Control a Vast Population of Nonspecific Cells: a Tale of Smart Bombs and the Infantry.* [Review]. Proc Natl Acad Sci USA 1996: 93: 2253–6: Hafler D A, Saadeh M G, Kuchroo V K, Milford E, Steinman L. *TCR Usage in Human and Experimental Demyelinating Disease.* [Review]. Immunol Today 1996; 17: 152–9). Using previously established structural criteria for T-cell-stimulating epitopes, an extensive database search identified 129 viral and bacterial candidate peptides that matched the structural features (not necessarily the sequence) of the predicted molecular mimicry motif of this MBP region (Wucherpfenning K W, Strominger J L. *Molecular Mimicry in T Cell Mediated Autoimmunity: Viral Peptides Activate Human T Cell Clones Specific for Myelin Basic Protein*. Cell 1995; 80: 695–705). Of these candidate peptides, seven viral and one bacterial peptide could indeed efficiently activate MBP-specific T-cell clones in vitro, although their primary amino acid sequence was quite different from MBP (Wucherpfenning K W, Strominger J L. *Molecular Mimicry in T Cell Mediated Autoimmunity: Viral Peptides Activate Human T Cell Clones Specific for Myelin Basic Protein*. Cell 1995; 80: 695–705). These results exemplify that a single TCR can recognize distinct, but structurally related, peptides from multiple pathogens, allowing for extensive cross-reactivity with seemingly unrelated antigens.

A different form of cross-relativity that could also lead to autoimmunity might occur at the level of the TCR. For a long time it was accepted dogma that each T cell (or T-cell clone) can express only one type of TCR, i.e., only one of the two alleles of the TCR Vα and Vβ chain is rearranged and functionally expressed (this phenomenon, which is also observed with Ig genes in B cells, is referred to as 'allelic exclusion'). There are, however, interesting exceptions. Allelic exclusion is not absolute for either the Vα and Vβ chain genes, and human T cells expressing two different TCR Vα (Padovan E, Casorati G, Dellabona P, Meyer S, Brockhaus M, Lanzavecchia A. *Expression of Two T Cell Receptor α Chains: Dual Receptor T Cells*. Science 1993; 262:422–4) or Vβ chains (Davodeau F, Peyrat M-A, Romangne F, Necker A, Hallet M-M, Vie H, et al. *Dual T Cell Receptor β Chain Expression on Human T Lymphocytes* J. Exp Med 1995; 181: 1391–8; Padovan E, Casorati G, Dellabona P, Meyer S, Brockhaus M, Lanzavecchia A. *Expression of Two T Cell Receptor α Chains: Dual Receptor T Cells*. Science 1993; 262:422–4) or Vβ chains (Davodeau F, Peyrat M-A, Romangne F, Necker A, Hallet M-M, Vie H, et al. *Dual T Cell Receptor β Chain Expression on Human T Lymphocytes* J. Exp Med 1995; Padovan E, Giachino C, Celia M, Valitutti S, Acuto O, Lanzavecchia A. *Normal T Lymphocytes Can Express Two Different T Cell Receptor β Chains: Implications for the Mechansim of Allelic Exclusion*. J Exp Med 1995; 181: 1587–91) have been described. In such T cells, one Vβ (or one Vα) chain would be expressed along with two Vα (or two Vβ) chains so that two types of αβ TCR could form and appear on the cell surface. If one the two receptors was specific for say, a bacterial antigen and the other for an autoantigen, and the T cell became activated during a bacterial infection, then the activated antibacterial T cells would represent activated autoantigen-specific T cells that could trigger an autoimmune attack against the antigen recognized by their second (autorcactive) αβ TCR.

Furthermore, potentially autoaggressive T cells could be activated in the periphery by stimulation with a viral or bacterial "superantigen." Superantigens stimulate T cells by cross-linking their TCR β-chain with an HLA class II molecule expressed on another cell (Marrack P, Kappler J, *The Staphylococcal Enterotoxins and Their Relatives* [published erratum appears in Science 1990: 248: 1066][see comments]. [Review]. Science 1990; 248: 705–11. Comment in: Science 1990;248:685–6; Kotzin B L, Leung D Y M, Kappler J, Marrack P. *Superantigens and Their Potential Role in Human Disease*. [Review]. Adv. Immunol 1993;54:99–166; Scherer M T, Ignatowicz L, Winslow G M, Kappler J W, Marrack P. *Superantigens: Bacterial and Viral Proteins That Manipulate the Immune System*. [Review]. Annu Rev Cell Biol 1993: 9:101–28; Fleischer B, *Superantigens*. [Review]. APMIS 1994; 102: 3–12). Because the superantigen-binding site of the TCR β-chain is shared between many different T-cell clones, superantigens can activate large numbers of T-cell clones specific for many different antigens, including autoantigens. Thus, superantigens could initially activate (or later reactivate) autoimmune T cells expressing a particular Vβ chain. This concept may be relevant to multiple sclerosis and has been indirectly supported by animal experiments in which relapses and exacerbations of Experimental Autoimmune Encephalomyeltis (EAE) could be induced with staphylococcal superantigens (for review, see Brocke S, Veromaa T, Weissman I L, Gijbels K, Steinman L. *Infection and Multipple Sclerosis: A Possible Role for Superantigens*? [Review]. Trends Microbiol 1994; 2:250–4). It should be noted, however, that injection of the same superantigens into naive (nonprimed) mice did not induce any signs of EAE (Brocke S, Veromaa T, Weissman I L, Gijbels K, Steinman L. *Infection and Multipple Sclerosis: A Possible Role for Superantigens*? [Review]. Trends Microbiol 1994; 2:250–4). This would not support a role of superantigens as the initial trigger of multiple sclerosis, but would be consistent with their participation in later stages.

Apart from activation by molecular mimicry, dual TCR expression, or superantigens, autoreactive T cells could also be stimulated by completely nonspecific mechanisms, such as the exposure to high local concentrations of cytokines secreted in the course of unrelated inflammatory reactions. Furthermore, loss of self-tolerance could result from a change in autoantigen expression or breakage of an anatomical barrier. Experimental support has been provided for most of these mechanisms, and it is likely that different human autoimmune diseases are triggered by different mechanisms. In addition, different mechanisms may operate at different stages of the same disease.

Whatever the exact mechanism of the initial activation of autoreactive T cells and their subsequent reactivation during relapses, it is likely that his activation occurs outside the CNS. As discussed in detail below, the CNS microenvironment has a strong tendency to reduce and limit local immune reactions, and therefore is not a likely site for autosensitization. This notion, derived mainly from animal experiments, is indirectly supported by MRI findings in multiple sclerosis demonstrating that brain and spinal cord lesions often occur concurrently (Thorpe J W, Kidd D, Moseley I F, Kenndall B E, Thompson A J, MacManus D G, et al. *Serial Gadolinium-enhanced MRI of the Brain and Spinal Cord in Early Relapsing-Remitting Multiple Sclerosis*. Neurology 1996; 46:378–8), strongly implicating a systemic trigger for disease activity.

Figure 7:
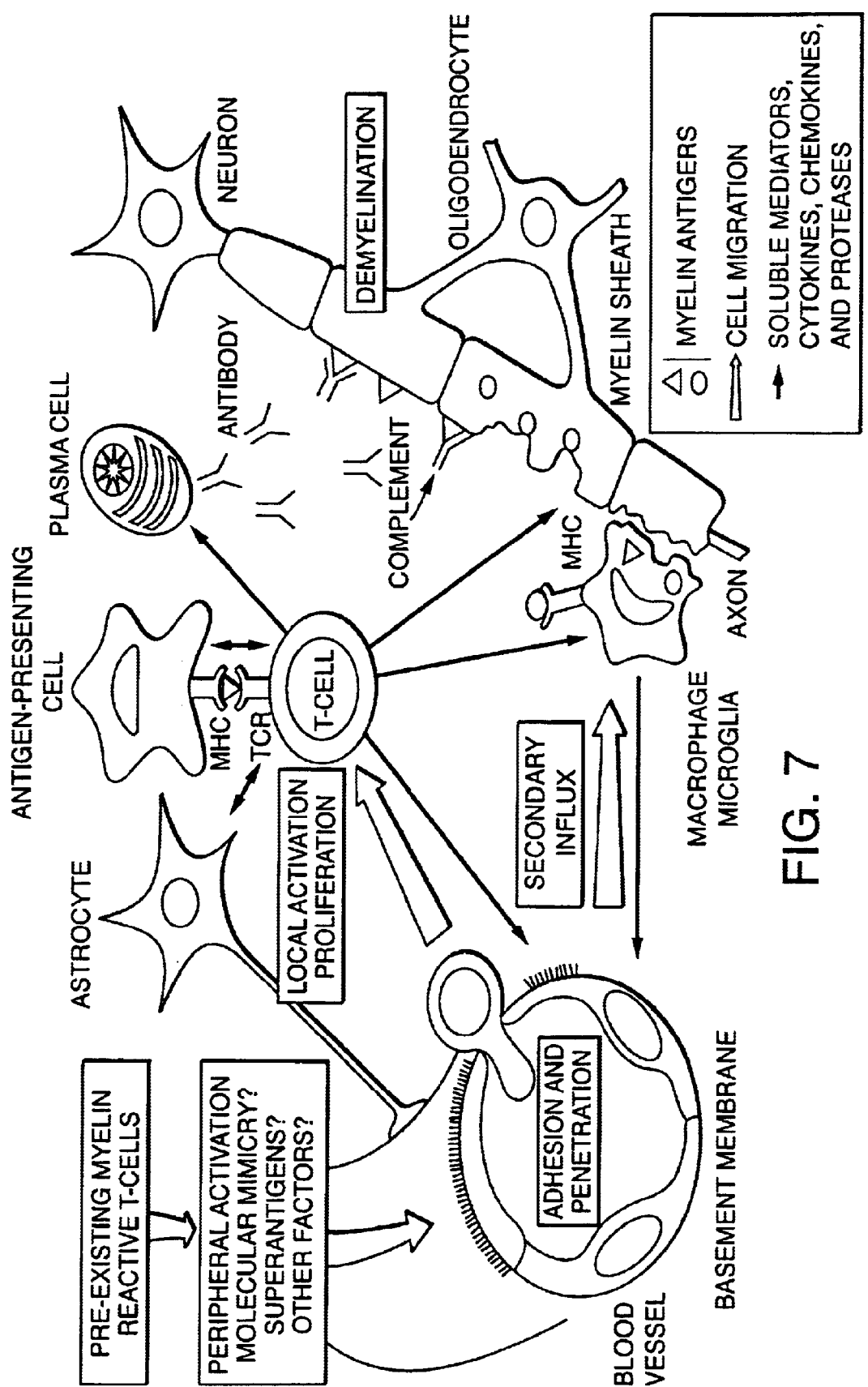
FIG. 7 presents a schematic of MS pathogenesis.

Once the autoantigen-specific, pathogenic T cells have been activated, they must find their way into the CNS (See, FIG. 7). Although it is firmly established that the blood-brain barrier is impermeable for circulating large molecules and for most cells, there is compelling evidence that activated T cells can enter the CNS irrespective of their antigen specificity (Wekerle H, Linington C, Lassmann H, Meryermann R. *Cellular Immune Reactivity Within the CNS*. [Review]. Trends Neurosci 1986: 9:271–7). Viewed teleologically, the selective properties of the barrier make sense. Consider the case of a systemic infection with a potentially neurotrophic virus, e.g. herpes simplex virus. T cells specific for viral determinants will be stimulated and activated in the periphery. This endows them with the capacity to traverse the blood-brain barrier so that they can scan the CNS for the presence of the virus. Thus, the CNS is by no means a 'blind spot' of the immune system but an area constantly surveilled by T cells engaged in an ongoing infection. If the T cells encounter 'their' foreign antigen in the CNS, they will eliminate it. Problems could arise only if the activated T cells (cross-react against an autoantigen expressed in the CNS. In this case, the local recognition of autoantigen by T cells may initiate a vicious circle of immunopathological reactions.

Upon activation, T cells increase their expression of "adhesion molecules", and this allows them to attach to endothelial cells expressing the appropriate counter-receptors (Butcher E C, Picker L J. *Lymphocyte Homing and Homeostasis*. [Review]. Science 1996; 272:60–6). Endothelial cells can express tissue-specific ligands, thereby guiding T cells to specific sites, depending on the particular combination of adhesion receptors expressed on the T cells and endothelial cells, respectively (Butcher E C, Picker L J. *Lymphocyte Homing and Homeostasis*. [Review]. Science 1996; 272:60–6). the extravasation of leukocytes is thought to occur in four steps. The first of these is mediated by selectins, which recognize carbohydrate epitopes of glycoproteins. Selectin-mediated adhesion is weak, and allows leukocytes to roll along the vascular endothelial surface. The second step depends upon interactions between the leucocyte integrins, e.g. leucocyte function-associated antigen (LFA-1), with molecules on endothelium such as the Ig-related molecule, intercellular adhesion molecule (ICAM)-1. This binding arrests the rolling and allows the leucocyte to attach firmly to the endothelium.

In the third step the leucocyte squeezes through the endothelial wall (diapedesis). The fourth step is the migration of the leukocytes through the tissues along a concentration gradient of chemoattractant molecules (chemokines) secreted by cells at the site of inflammation. It is clear that the various adhesion molecules involved in the extravasation process are potential target for immunotherapy.

Once having entered the brain, the activated autoreactive T cells must be confronted with CNS autoantigens within the CNS parenchyma. Animal experiments in which experimental autoimmune encephalomyelitis (EAE) can be transferred into previously healthy recipients by the injection of activated CD4+, MBP-specific, T cells (for review, see Wekerle et al., 1994) indicate that the first intruders are autoantigen-specific CD4+ T cells, CD4+ cells recognize their antigen as peptides embedded in MHC class II molecules located on the membranes of antigen-presenting cells.

Like all immunological reactions, the recruitment of local antigen-presenting cells must be considered as a dynamic process. A few strategically localized antigen-presenting cells, constitutively expressing MHC class II together with sufficient myelin peptides released from adjacent oligodendrocytes and myelin sheaths during physiological turnover, may be sufficient to stimulate some of the arriving CD4+ autoreactive T cells (See, FIG. 7). These T cells are reactivated, produce more proinflammatory mediators, and soon other local cells will be recruited to express MHC class II and co-stimulatory molecules (for review, see Shrikant P, Benveniste E N. *The Central Nervous System as an Immunocompetent Organ. Role of Glial Cells in Antigen Presentation*. [Review]. J Immunol 1996; 157:1819–22). Thus, there is a hierarchy of inducibility of such "facultative" antigen-presenting cells; perivascular monocytes and microglia cells are activated first and most easily (some express MHC class II molecules seven constitutively), and activation of other microglia cells, pericytes and perhaps endothelial cells and astrocytes follows (Vass K, Lassmann H. *Intrathecal Application of Interferon Gamma. Progressive Apperance of MHC Antigens within the Rat Nervous System*. Am J Pathol 1990; 137: 789–800; Lassmann H, Rossler K, Zimprich F, Vass K. *Expression of Adhesion Molecules and Histocompatibility Antigens at the Blood-Brain Barrier*. [Review]. Brain Pathol 1991a; 1:115–23; Lassmann H, Zimprich F, Rossler K, Vass K. *Inflammation in teh Nervous System. Basic Mechanisms and Immunologoical Concepts*. [Review] Rev Neurol (Paris) 1991b; 147:763–81; Lassmann H, Zimprich F, Vass K, Hickey W F. *Microglial Cells are a Component of the Perivascular Glia Limitans*. J Neurosci Res. 1991c; 28: 236–43; Fabry Z, Raine C S, Hart M N. *Nervous Tissue as an Immune Compartment: the Dialect of the Immune Response in the CNS*. [Review] Immunol Today 1994; 15:218–24).

Once the inflammatory reaction has been fully ignited, the local brain microenvironment will change rapidly. The concentrations of inflammatory mediators rise sharply, leading to changes in the blood-brain barrier and allowing a secondary influx of monocytes and other inflammatory cells (See, FIG. 7). During the different stages of acute and chronic lesions, different cells may play different roles. This is exemplified by the complex role of astrocytes. In some situations, cytokine-stimulated astrocytes might act as fully competent (Fontana A, Fierz W, Werkle H. *Astrocytes Present Myelin Basic Protein to Encephalitogenic T Cell Lines*. Nature 1984; 307:273–6) or partially competent (Weber F, Meinl E, Aloisi F, Nevinny-Stickel C, Albert E, Werkerle H, et al. *Human Astrocytes are only Partially Component Antigen Presenting Cells: Possible Implications for Lesion Development in Multiple Sclerosis*. Brain 1994; 117: 59–69) facultative antigen-presenting cells during an early stage of legion development. Under different conditions, however, the same astrocytes can produce local inhibitory signals that limit the activity of lesions during a later stage (Meinl E, Aloisi F, Ertl B, Weber F, de Waal Malefyt R, Wekerle H, et al. *Multiple Sclerosis: Immunomodulatory Effects of Human Astrocytes on T Cells*. Brain 1994; 117:1323–32 for review, see Shrikant P, Benveniste E N. *The Central Nervous System as an Immunocompetent Organ. Role of Glial Cells in Antigen Presentation*. [Review]. J Immunol 1996; 157: 18919–22).

An important lesson from EAE is that many proteins of the nervous system are potentially encephalitogenic. Apart from MBP, the autoantigen of classic EAE, other myelin antigens such as proteolipid protein (PLP) and myelin-oligodendrocyte glycoprotein (MOG) can all induce experimental encephalomyelitis under appropriate conditions. An experimental auto-immune encephalitis can even be induced with non-myelin antigens such as S100β, which is abundantly expressed in astroglia but not oligodendrocytes. Interestingly, any single autoantigen may produce different types of clinical course and pathology in different strains of the same animal species. Furthermore, the topography of lesions may be strictly dictated by the nature and origin of the autoantigen. Antigens present in the compact myelin, such as MBP and PLP, produce lesions located in areas with the thickest myelin sheaths (spinal cord and brainstem). In contrast, MOG, an antigen localized exclusively on the myelin surface, is present in high concentrations in area with many thin myelin sheaths. The sites of inflammation observed after transfer of MOG-specific T cells include the periventricular and cerebellar white matter. The inflammation induced by S100β-specific T cells involves the cerebral cortex, retina and uvea in addition to the typical white matter lesions (Kojima K, Berger T, Lassmann H, Hinze-Selch D, Zhang Y, Gehrmann J, et al. *Experimental Autoimmune Panencephalitis and Uveoretinitis Transferred to the Lewis Rat by T Lymphocytes Specific for the S100β Molecule, a Calcium Binding Protein of Astroglia*. J Exp IMed 1994: 180:817–29). The cellular composition of the infiltrates also varies between the different EAE modes. For example, the lesions are composed predominantly of T cells in S100β-induced disease, whereas activated macrophages predominate in MBP-induced EAE lesions.

Translated to multiple sclerosis pathogenesis, these observations could help to explain the heterogeneity of the disease. Like in EAE models, heterogeneity could reflect individual patterns in response to the same antigen, or a variable response to different antigens, or both. The situation is further complicated by the possibility that different autoantigens might be involved during different stages of multiple sclerosis.

While the immunopathogenesis of multiple sclerosis based on autoreactive T cells has been considered above, additional data suggests that B cells and their products (antibodies) are equally important vis-a-vis demyelination. The lesions of classic the MBP-induced EAE in Lewis rats, which are produced by the transfer of purified MBP-specific T cells alone, are mainly inflammatory, not demyelinating. If, however, a myelin-oligodendrocyte glycoprotein (MOG) specific monoclonal antibody is co-injected with the T cells, large demyelinating lesions develop (Linington C, Bradl M, Lassmann H, Brunner C, Vass K. *Augmentation of Demyelination in Rat Acute Allergic Encephalomyelitis by Circulating Mouse Monoclonal Antibodies Directed Against a Myelin/Oligodendrocyte Glycoprotein*. Am J. Pathol 1988; 130:443–54; Genain C P, Nguyen M-H, Letvin N L, Pearl R, Davis R L, Adelman M, et al. *Antibody Facilitation of Multiple Sclerosis-Like Lesions in a Nonhuman Primate*. J Clin Invest 1995a; 96: 2966–74). That the transfer of T cells is necessary, but by no means sufficient for demyelination, has not only been observed with MBP-specific T cells but also with T cells specific for other CNS autoantigens, such as MOG and S-100β. Also in those models, demyelinating lesions develop after co-injection of anti-MOG antibody (Linington C, Berger T, Perry L, Weerth S, Hinze-Selch D, Zhang Y, et al. *T Cells Specific for the Myelin Oligodendrocyte Glycoprotein Mediate and Unusual Autoimmune Inflammatory Response in the Central Nervous System* Euro J immunol 1993; 23:1364–72; Kojima K, Berger T, Lassmann H, Hinze-Selch D, Zhang Y, Gehrrmann J, et al. *Experimental Autoimmune Panencephalitis and Uveoretinitis Transferred to the Lewis Rat by T Lymphocytes Specific for the S100β Molecule, a Calcium Binding Protein of Astroglia*. J Exp Med 1994; 180:817–29). These observations support the concept that T cells specific for various CNS autoantigens initiate inflammation and open the blood brain barrier, whereas autoantibodies against surface antigens of myelin or oligodendrocytes are pivotal to demyelination.

Furthermore, autoreactive helper T cells might locally cooperate with B cells in the production of anti-myelin autoantibodies, especially in chronic lesions. (see Ozawa K, Suchanek G, Breitschophf H, Bruck W, Budka H, Jellinger K, et al. *Petterns of Oligodendroglia Pathology in Multiple Sclerosis*. Brain 1994; 117:1311–22). Locally produced Igs are presumably enriched in autoantibodies, because autoantigen-specific T cells, autoantigen-specific B cells, antigen-presenting macrophages and glial cells, and autoantigen are all concentrated in the same local microenvironment. In addition to locally produced Igs, systemically produced antibodies could gain access to the CNS when the blood-brain barrier becomes leaky as a consequence of local inflammation.

Finally there is evidence that after finding to the myelin surface, demyelinating autoantibodies activate complement and attract macrophages/microglia. The macrophages contribute to demyelination not only by physically 'stripping' the myelin but also by directed release of complement and inflammatory mediators, including reactive oxygen species and eieosanoids. See, Hohlfeld, R., Biotechnological Agents For The Immunotherapy Of Multiple Sclerosis, Brain, 120, pp. 865–916 (1997).

The practice of the present invention is not dependent on the complete elucidation or understanding of any of the proposed immuno-reactive scenarios. However, these data serve as background for embodiments of the present invention which are directed to the detection of antibodies against brain ferritin binding protein in the brain as a diagnostic method for multiple sclerosis. In another embodiment, the present invention contemplates the generation and purification of antibodies against said brain ferritin binding protein. In another embodiment, the present invention contemplates the generation and purification of antibodies against a portion of said brain ferritin binding protein. In another embodiment, the present invention contemplates binding said ferritin receptor with ferritin and the subsequent reaction of said receptor-ferritin complex with the sera from a patient suspected of having MS under conditions such that any shift in the ferritin-receptor complex may be observed.

EXPERIMENTAL

The following examples serve to illustrate certain embodiments and aspects of the present invention and are not to be construed as limiting the scope thereof.

Example 1

Iodination of Iron Binding Proteins

Holo-transferrin (Sigma) and recombinant H-chain ferritin (rH-ferritin) were iodinated via the chloramine-T method. Specific activities of iodinated proteins ranged from 6,000–17000 dpms/ng protein. Binding studies were performed within 2 weeks of iodination to avoid protein degradation.

Example 2

Origin of Experimental Tissue

The human tissue used to generate data presented through the instant application was frozen immediately subsequent to harvest from postmortem or surgical pathological specimens. The tissue was selected from individuals who died of non-neurological conditions and from individuals with a confirmed diagnosis of Multiple Sclerosis. Aged matched control (n=4) and MS tissue (n=4), which included periventricular white matter, were obtained from the Harvard Brain Tissue Research Center. Macroscopic lesions were observed in the MS tissue. Additional control brain tissue was obtained postmortem (n=3) from autopsies (at the Milton S. Hershey Medical Center) or from temporal lobe specimens (n=3) obtained during temporal lobectomy for intractable seizures. The surgical tissue was used only for autoradiography.

Example 3

Autoradiography

Control, lobectomized and multiple sclerotic brain sections were cut at 10 micron thickness on a cryostat, thawmounted on chrome alum coated slides and stored at −80° C. Some sections were counterstained with hematoxylin and eosin for cytological analysis and histopathological evaluation (including confirmation of MS lesion sites). The ideal concentration of ferritin for autoradiography was determined empirically from the binding studies. The concentration of transferrin was chosen based on published reports for rat tissue. Tissue sections were overlaid with either 4 nM $^{125}$I rH-ferritin or 4 nM $^{125}$I holo-transferrin in a binding buffer of 200 mM Sucrose, 50 mM HEPES and 1% bovine serum albumin. Incubation was performed for one hour at 22° C. before being terminated by 4 successive 5 minute rinses in ice-cold 0.1 M phosphate buffered saline (pH 7.4). Slides were allowed to air dry before being apposed to KODAK autoradiography film for 7($^{125}$I rH-ferritin) or 14 ($^{125}$I Tf) days. The periods of exposure were determined empirically to equilibrate differences in specific activities of iodinated transferrin and rH-ferritin.

Example 4

Membrane Preparations

Sections of either corpus callosum or cortical white matter were thawed on ice in 100 volumes of cold 50 mM Tris, pH 7.4. The thawed brains were homogenized for 1 minute using a Janke and Kunkel Ultra Turrax T25 tissue homogenizer. The homogenate was centrifuged at 29000×g for 10 minutes at 4° C. The supernatant was aspirated and the membrane pellet was resuspended in the original volume of buffer. The homogenate was then recentrifuged at 29000×g for 10 minutes at 4° C. The supernatant was removed and the membrane pellet was resuspended in 4 mls of 50 mM Tris, pH 7.4. Protein concentrations were determined by the BioRad assay.

Example 5

Kinetics Study

Duplicates of membrane preparations (prepared according to the protocol presented in Example 4) from 3 different control human brain samples were incubated at 22° C. with 0.2 nM $^{125}$I rH-ferritin for up to 100 minutes. The binding suspension consisted of 50 mM Tris, 0.1% BSA, 5 mM HCl and 25 µgs membrane protein preparation with or without the addition of 1 µM unlabeled rH-ferritin (the latter for non-specific binding) in a final volume of 400 µls. The reaction was terminated by the addition of 3 mls of ice cold 50 mM Tris, pH 7.4. Bound radioactivity was isolated by rapid filtration over Whatman glass fiber C filters that had been previously coated in a solution of 5% non-fat dried milk with 0.1 mg/ml horse spleen ferritin (Sigma). This combination was determined empirically to reduce the non-specific binding of radiolabeled protein to the filters to 1–3% of the total counts added (Hulet et al, in press). The filters were washed 4× with 3 mls of ice cold 50 mM Tris containing 200 mM NaCl. The filters were dried under a heat lamp before being counted in a Gamma Trac gamma counter (76.57% efficiency). Specific binding was calculated by subtracting binding in the presence of excess unlabeled rH-ferritin (nonspecific binding) from binding in the absence of excess unlabeled rH-ferritin (total binding).

Example 6

Saturation Analysis

A total of 4 different control human brain samples were used for these experiments. Each binding experiment was performed in duplicate. Increasing concentrations of $^{125}$I rH-ferritin were added to binding suspensions consisting of the same binding buffer described previously with 25 µgs membrane protein preparation with or without the addition of 1 µM unlabeled rH-ferritin in a final volume of 400 µls. Following a 60 minute incubation at 22° C. binding was terminated and total, nonspecific and specific binding was calculated as described above. The binding affinity and receptor density was determined using GraphPad Prism software.

Example 7

Competition Assay

Duplicates of membrane preparations (prepared according to the protocol presented in Example 4) from 3 different human brain sections were used in these experiments. Increasing concentrations of unlabeled rH-ferritin (15.625, 31.25, 62.5, 125, 250, 500, 750, 1000, 1250, 1500 or 2000 nM), horse spleen ferritin (150, 500, 1000, 1500 and 2000 nM) or human holo-transferrin (150, 500, 1000, 1500 and 2000 nM) were incubated for 60 minutes at 22° C. with 25 µgs membrane protein in the presence of 0.2 nM $^{125}$I rH-ferritin in the same binding buffer described previously. Binding, termination of binding, isolation of membranes and calculations of specific activity were performed as described.

Example 8

Immunocytochemistry

Tissue sections containing MS lesions which were contiguous to those used for the autoradiographic studies were immunoreacted with a polyclonal antibody to the human transferrin receptor. The sections were exposed to primary antibody (1:100) overnight at 4° C. The secondary and tertiary antibodies (1:100) were applied for 1 hour at room temperature. The reaction product was visualized using 3,3'diaminobenzide (DAB) according to our standard protocols.

Example 9

In Situ Cerebral Ferritin Binding

To demonstrate the presence of ferritin binding sites in the human brain, binding studies were performed, using iodinated human recombinant heavy chain ferritin (rH-ferritin) and membrane preparations isolated from postmortem adult human brain sections. Total binding was consistently <10% of total DPMs added. Specific binding ranged from 60–85% of total binding. The association rate of $^{125}$I rH-ferritin (0.2 nM) was examined by measuring specific binding over a 100 minute period. A steady state of binding was reached by 45 minutes (FIG. 1) with only a slight reduction in specific binding observed at 100 minutes. Thus, incubations were carried out for 60 minutes to ensure equilibration of assay components.

Figure 2:
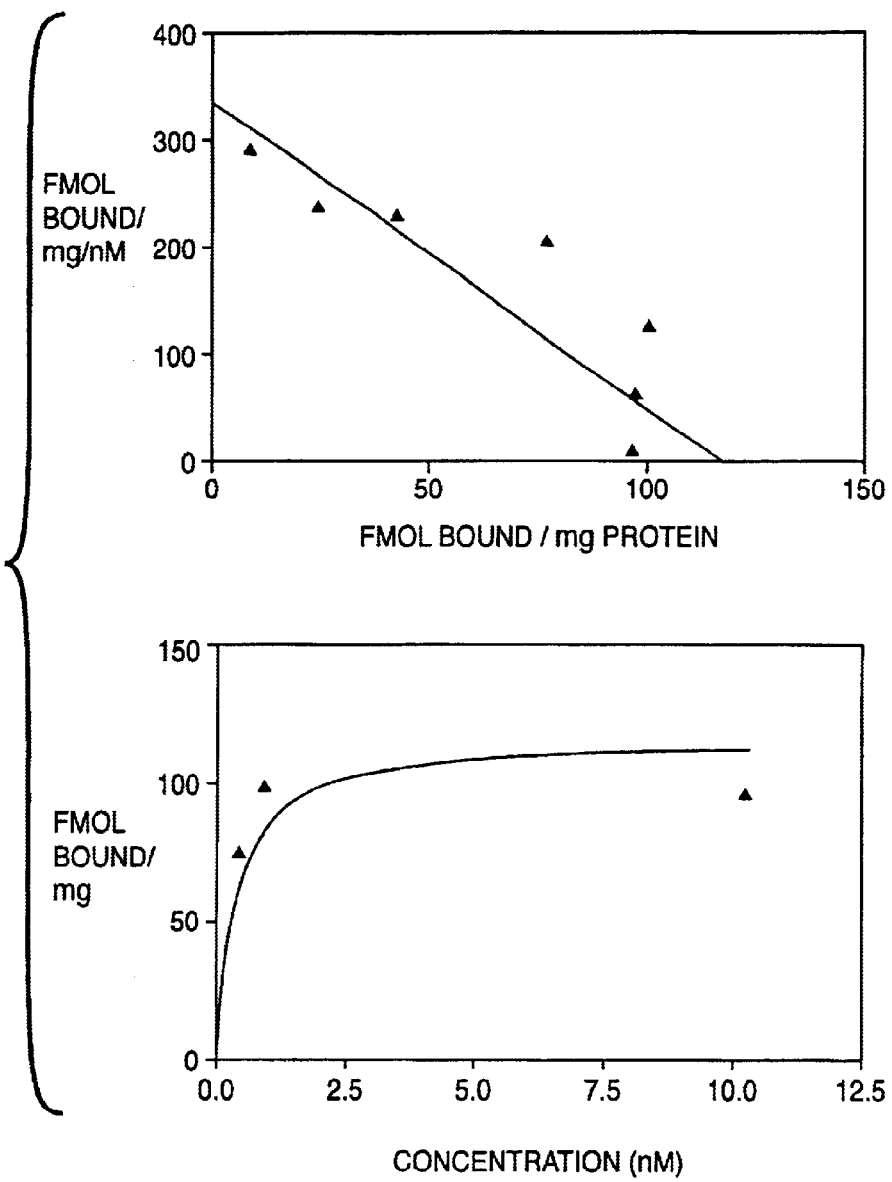
FIG. 2 presents a saturation analysis (inset) shows that the binding of $^{125}$I rH-ferritin to human membrane homogenates is saturable. The saturation and Scatchard analysis shown is a representative analysis taken from one experiment (1 membrane preparation in duplicate) revealing a Kd of 0.35 nM and a Bmax of 116.7 fmol bound/mg protein. Binding experiments were performed on 4 different human brain homogenates.

Saturation analysis demonstrated specific and saturable binding of $^{125}$I rH-ferritin to human brain membrane preparations (FIG. 2 inset). Scatchard plots of saturation data (n=4) indicated a single binding site with a dissociation constant (Kd) of 0.35±0.06 SEM $10^{-9}$ M and a receptor density (Bmax) of 116.7±12.6 SEM fmol bound/mg protein.

Figure 3:
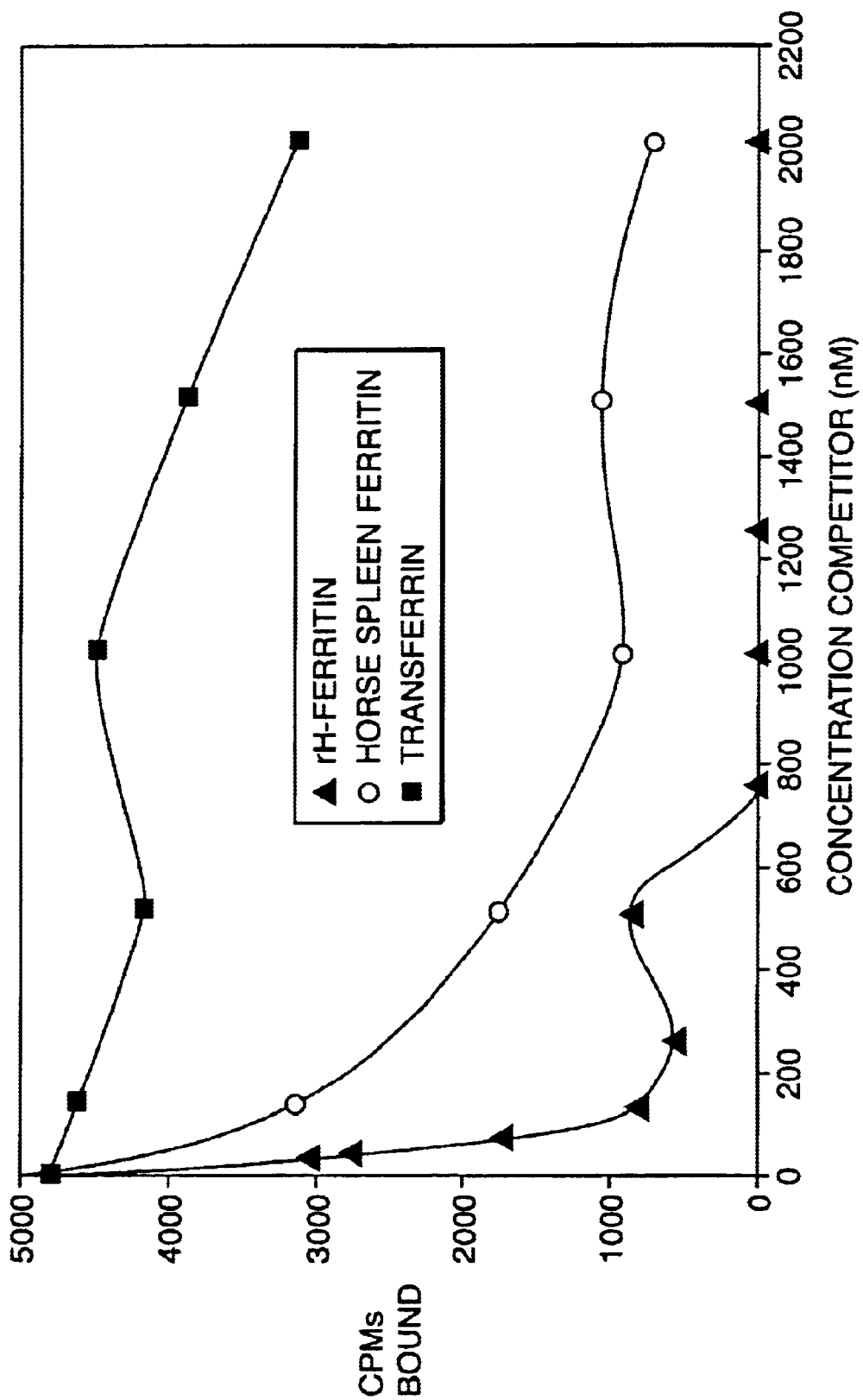
FIG. 3 presents data showing that the binding of $^{125}$I rH-ferritin (0.2 nM) to human membrane homogenates can be inhibited, in a concentration dependent manner, by incubating with excess amounts of horse spleen ferritin or rH-ferritin but not with excess human holo-transferrin. The curves are representative, taken from one experiment (1 membrane preparation in duplicate). Binding experiments were performed on 3 different human brain homogenates.

Excess rH-ferritin completely inhibited $^{125}$I rH-ferritin binding at 0.75 µM (FIG. 3). Excess horse spleen ferritin was able to inhibit approximately 80% of binding at a concentration of 1 µM. Excess transferrin did not inhibit binding of $^{125}$I rH-ferritin to the membrane preparations.

Example 10

Binding Distributions of Ferritin and Transferrin

Figure 4:
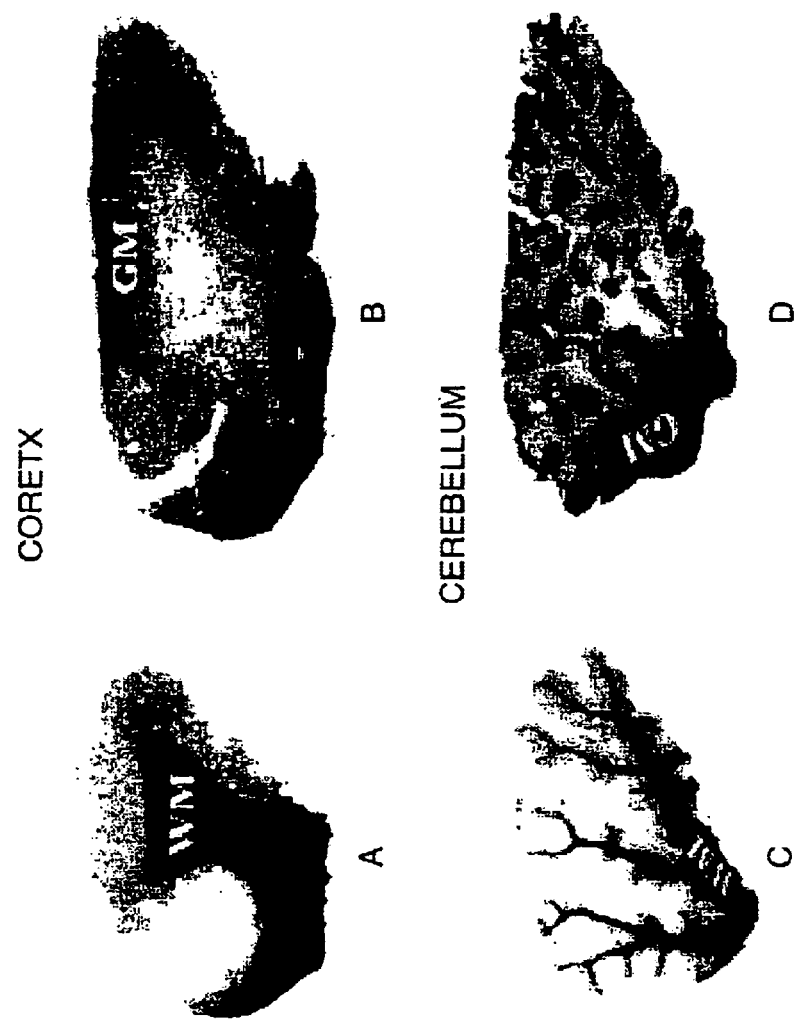
FIG. 4 presents binding distributions of $^{125}$I rH-ferritin (A&C) or $^{125}$I transferrin (B&D) in control brain sections. Sections from tissue specimens of 9 different brains obtained either as postmortem or surgical specimens were analyzed, with similar results. A&B: Motor Cortex C&D: Cerebellum. "WM" and "GM" represent white matter and gray matter areas respectively.

For the distribution analysis, tissue sections could be stored for up to 2 weeks with no noticeable loss in binding activity. No differences in ferritin or transferrin binding distributions were observed in postmortem v. operative tissue. FIG. 4 shows the results of binding distributions for $^{125}$I rH-ferritin and $^{125}$I human holo transferrin to contiguous sections from two regions of normal control brains. Ferritin binding distribution is primarily within white matter tracts in both cortex and cerebellum. Transferrin binding distribution is evident primarily within gray matter.

Figure 5:
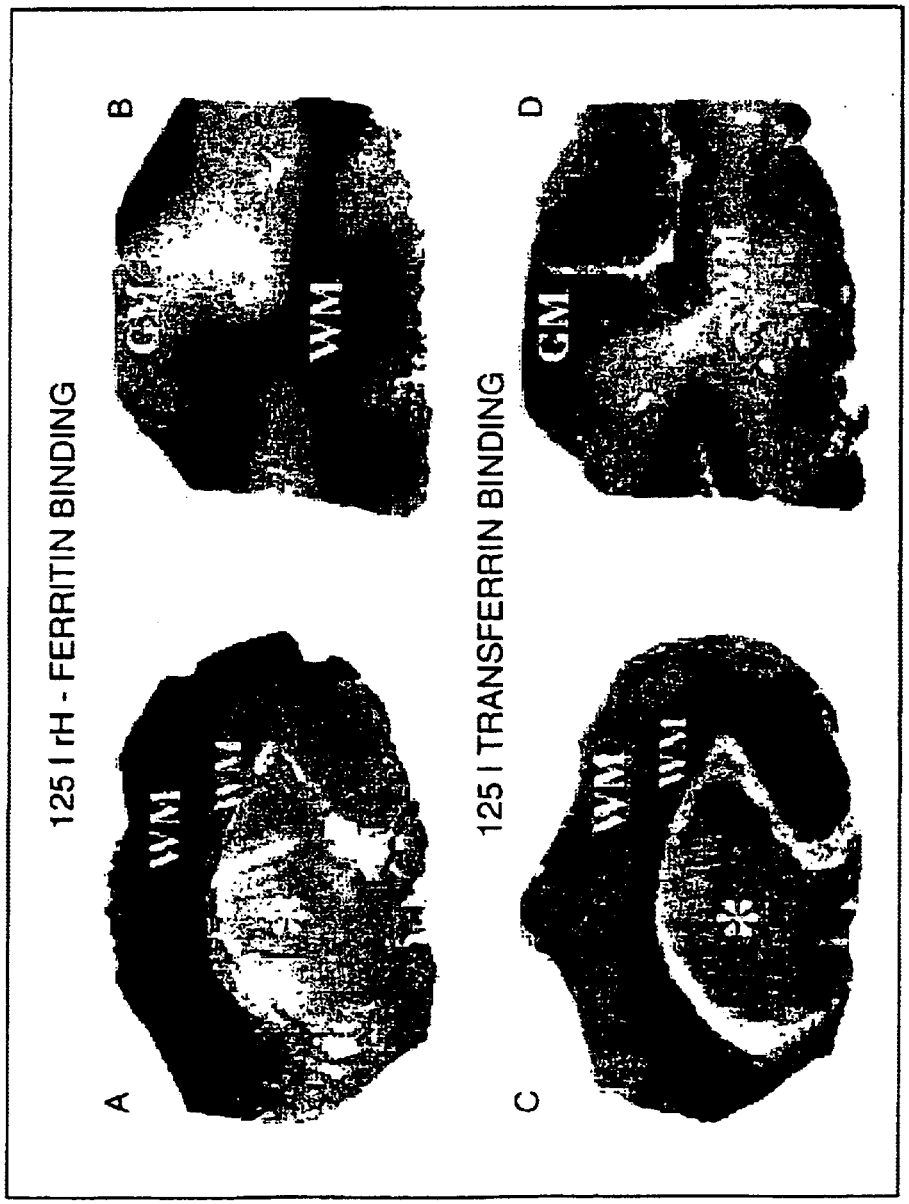
FIG. 5 presents binding distributions of 4 nM $^{125}$I rH-ferritin (A&B) and $^{125}$I human holo transferrin (C&D) to contiguous tissue sections from the brain of a patient with multiple sclerosis (representative example from analyses of plaques in three patients). "WM" and "GM" represent white matter and gray matter areas respectively. Images B&D show radiolabeled binding to nonplaque areas of MS tissue (temporal cortex with underlying white matter). Ferritin binding distribution is primarily within white matter which is consistent with ferritin binding observed in the brain sections from non-diseased controls (FIG. 4). Conversely, transferrin binding distribution is primarily within gray matter which is consistent with transferrin binding distributions seen in human brain sections from non-diseased controls (FIG. 4). Images A&C show sections from periventricular white matter with a large sclerotic lesion (indicated by the asterisk in the center of the lesion). In contrast to control tissue, transferrin binding is present in the periplaque white matter but ferritin binding is not.
Figure 6:
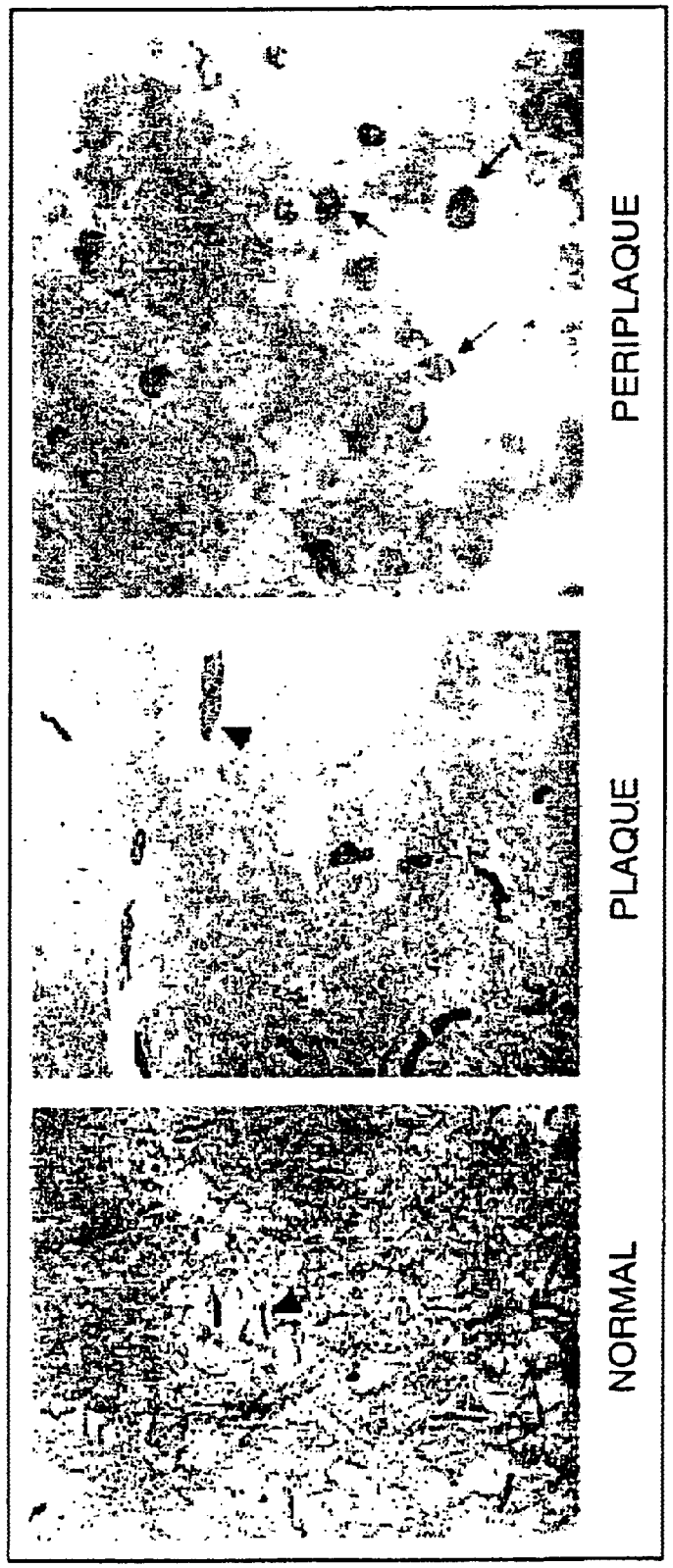
FIG. 6 presents a series of micrographs (at 625×) from MS human brain tissue which have been immunoreacted for transferrin receptor. The sections are contiguous with the sections in FIG. 5 (A and C). The "normal" section is from a non-plaque area of white matter in which immunoreactivity is only seen in blood vessels (e.g. arrowhead). Similarly, within the plaque, only blood vessels (arrowhead) immunoreact with transferrin receptor antibodies. In the periplaque region, transferrin receptor positive cells are seen (arrows). These cells are round, have eccentric nuclei, limited cytoplasm and few processes; this morphological description is consistent with that of oligodendrocytes.

A total of 4 different brains containing MS lesions were examined. In non-lesion areas $^{125}$I rH-ferritin binding was present in white matter regions and $^{125}$I transferrin binding was primarily in grey matter areas. However, in lesion containing white matter, $^{125}$I transferrin bound to the periplaque region. $^{125}$I rH-ferritin binding was not present in the periplaque region or within the lesion itself. Indeed the distributions of transferrin and ferritin binding in white matter periplaque regions were non-overlapping. FIG. 5 shows the binding distributions of $^{125}$I rH-ferritin and $^{125}$I human holo transferrin to representative tissue sections from the brain of a multiple sclerosis (MS) patient. The binding pattern returned to normal in the white matter as the distance from the lesion became greater. Transferrin binding surrounding the plaque area is evident only at the edges of the lesion, whereas no ferritin binding activity is present in the lesion or in the periplaque region. The presence of transferrin receptor positive cells in the periplaque region was confirmed immunocytochemically and these cells are morphologically similar to oligodendrocytes (FIG. 6).

Example 11

Ferritin Binding by Brain Protein

Figure 9:
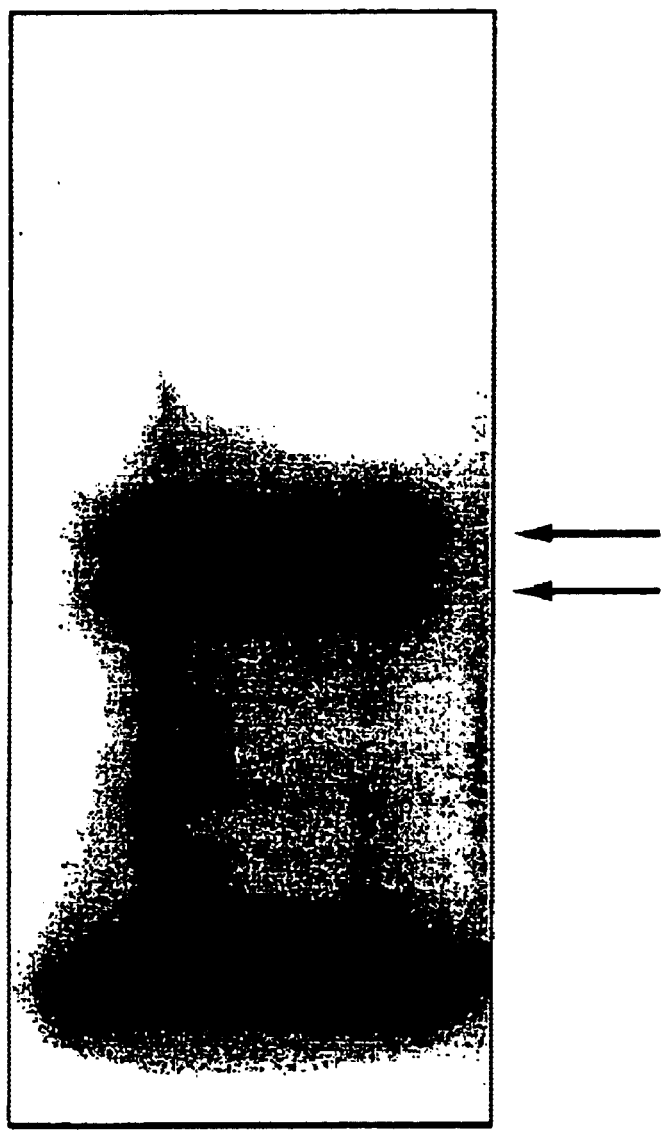
FIG. 9 presents an (approximate) 55 kd ferritin binding protein isolated from brain homogenate, separated using native PAGE (7.5% gel).

Intact mouse brains were harvested and homogenized in a physiological buffer. Proteins in the resulting homogenate were separated using native PAGE (7.5% gel). The resolved proteins were transferred from the gel to a nitrocellulose membrane according to standard methods. The "transferred" nitrocellulose membrane was incubated with iodinated ferritin prepared according to the methods set out in Example 1. The membrane treated under conditions such that substantially all of the unbound iodinated ferritin was removed and was subsequently exposed to film to visualize the proteins that bound the labeled ferritin. These data are presented in FIG. 9 wherein a strong signal from a single band, corresponding to 55 kD relative to molecular weight standards (data not shown), is shown.

Example 12

IRE/IRP Gel Shifts

Cytosolic protein samples from various treatment groups (control, iron treated, ferritin treated, desferal treated) were prepared for gel electrophoresis with 5 µg of cytosolic protein in a volume of 10 mls with or without the addition of 2 µls of P-mercaptoethanol (Sigma). The samples were incubated at 22° C. for 5 minutes before the 32P-IRE probe was added. The reaction was terminated after 15 minutes with the addition of 2 µls of running dye. The proteins were gel electrophoresed (6% polyacrylamide gel), the gel was dried and apposed to autoradiography film overnight.

Figure 8:
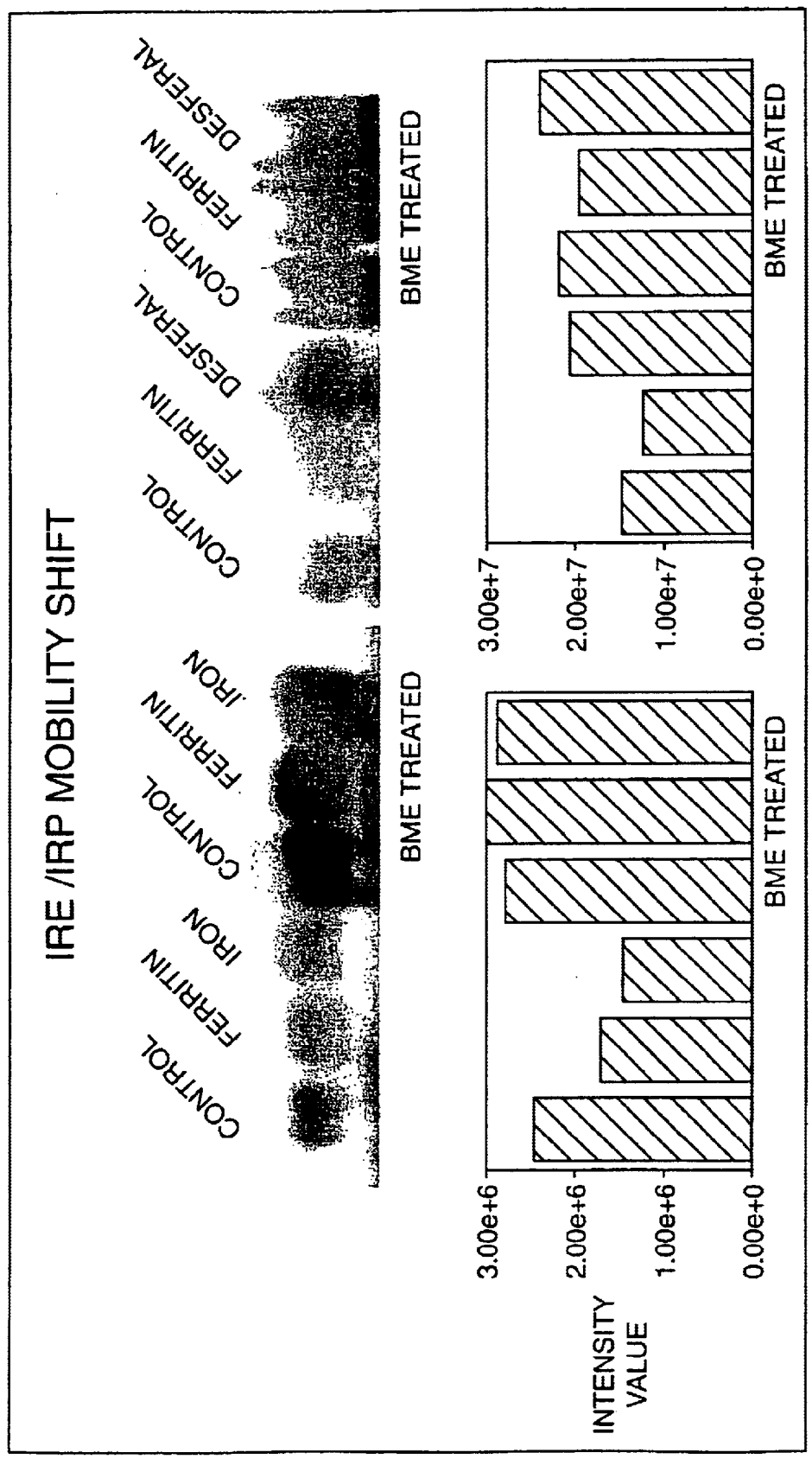
FIG. 8 presents data on the effects of ferritin, iron and desferal treatments on intracellular labile iron pool.

Turning to the data presented in FIG. 8, incubating oligodendrocyte progenitor cells in ferritin (5 nM) for 16 hours resulted in an approximate 10% decrease in the binding of a 32P-labeled mRNA fragment containing an iron responsive element (IRE) to the mRNA binding iron regulatory protein (IRP) a cytosolic MRNA binding protein as compared to controls. A similar decrease in IRE/IRP binding to that seen with ferritin exposure was observed when the cells were treated with ferric ammonium citrate (FAC 100 µg/mL). Pretreatment of the cells with 100 µM desferal (DFO) for 16 hours resulted in an increase (2 fold) in IRE/IRP binding activity.

Three separate experiments were performed for each treatment. The top panel is a representative gel shift assay. The bottom bar graph shows composite data analysis for 3 separate experiments. Intensity values (bar graph) were assessed by scanning the images into Collage (Photodyne, Inc.) and performing each data analysis in triplicate. The data were then converted into intensity values as a percentage of control intensity values. The means +/−standard error are shown on the bar graphs.

It is significant to note, that β-mercaptoethanol (BME) treated cell extracts allow for all of the IRP present to be available to bind $P^{32}$-IRE. Therefore BME treated extracts present a measure of the total IRP. By extension, cell extracts not treated with BME present a measure of available IRP (e.g. that fraction not already bound to endogenous IRE) thereby providing a basis to compare total IRP v. available IRP.

Example 13

Purification of Ferritin Binding Protein

The present invention contemplates methods whereby the ferritin binding protein (as described in Example 11) is purified. In one example, an affinity matrix will be prepared comprising a ligand bound to an inert support by a chemical bond between a primary amine group on the protein and an activated group on the support. It is not intended that the present invention be limited to a specific purification method. However, in one embodiment Ferritin labeled Avidin (Sigma, product No. A 5405) incubated with Biotinylated Acrylic Beads (Sigma, product No. B 3272), in a physiological buffer, under conditions such that said Biotinylated beads are substantially bound with said Ferritin labeled Avidin. This Ferritin/Avidin/Biotin/Acrylic Bead column complex is equilibrated with buffer prior to loading with the homogenate described in Example 11. After said homogenate is eluted, unbound protein is washed from the column with an appropriate buffer. The Ferritin binding protein bound to said column complex is then eluted from the column with any number of dissociation buffers well described in the art. In some embodiments of the present invention, this eluted Ferritin binding protein may be concentrated. If necessary, the protein solution is then concentrated using an ultrafiltration apparatus (Amicon).

In another embodiment, affinity chromatography will be performed using a poly-hisitidine tagged proteins for creation of protein affinity columns. The histidine tag is very short (10 his residues) and will not alter the conformation of the tagged protein, nor should will it be involved in artifactual interactions. The poly-his tag binds to a nickel chelate resin for creation of the column. This resin will be used alone for the control columns. Other affinity purification methods would also be suited to the purification of ferritin binding protein. See, Ausubel et al. (eds.), Current Protocols in Molecular Biology, John Wiley & Sons, Inc., New York, "Immunoaffinity Chromatography, pp. 10.11.1–10.11.9 [1994].

Example 14

Preparation of Antibody Against Ferritin Binding Protein

The present invention contemplates methods whereby antibodies against Ferritin binding protein (as prepared in Example 13, in one example) are prepared. It is not intended that the present invention be limited by the method of antibody production. In one embodiment, however, antibodies will be prepared according to the following methods.

Both polyclonal and monoclonal antibodies are obtainable by immunization with the Ferritin Binding Protein and either type is utilizable for immunoassay. The methods of obtaining both types of are well known in the art. Polyclonal sera are less preferred but are relatively easily prepared by injection of a suitable laboratory animal with an effective amount of the purified enzyme or protein, or antigenic parts thereof, collecting serum from the animal, and isolating specific sera by any of the known immunoadsorbent techniques. Although antibodies produced by this method are utilizable in virtually any type of immunoassay, they are generally less favored because of the potential heterogeneity of the product.

The use of monoclonal antibodies in an immunoassay is particularly preferred because of the ability to produce them in large quantities and the homogeneity of the product. The preparation of hybridoma cell lines for monoclonal antibody production derived by fusing an immortal cell line and lymphocytes sensitized against the immunogenic preparation can be done by techniques which are well known to those who are skilled in the art. (See, for example Douillard and Hoffman, Basic Facts about Hybridomas, in *Compendium of Immunology* Vol II, ed. by Schwartz, 1981; Kohler and Milstein, *Nature* 256: 495–499, 1975; *European Journal of Immunology* 6: 511–519, 1976).

Unlike preparation of polyclonal sera, the choice of animal is dependent on the availability of appropriate immortal lines capable of fusing with lymphocytes. Mouse and rat have been the animals of choice in hybridoma technology and are preferably used. Humans can also be utilized as sources for sensitized lymphocytes if appropriate immortalized human (or nonhuman) cell lines are available. For the purpose of the present invention, the animal choice may be injected with an antigenic amount, for example, from about 0.1 mg to about 20 mg of the enzyme or protein or antigenic parts thereof. Usually the injecting material is emulsified in Freund's complete adjuvant. Boosting injections may also be required.

A number of cell lines suitable for fusion have been developed and the choice of any particular line for hybridization protocols is directed by any one of a number of criteria such as speed, uniformity of growth characteristics, deficiency of its metabolism for a component of the growth medium, and potential for good fusion frequency.

Intraspecies hybrids, particularly between like strains, work better than interspecies fusions. Several cell lines are available, including mutants selected for the loss of ability to secrete myeloma immunoglobulin.

Cell fusion can be induced either by virus, such as Epstein-Barr or Sendai virus, or polyethylene glycol. Polyethylene glycol (PEG) is the most efficacious agent for the fusion of mammalian somatic cells. PEG itself may be toxic for cells and various concentrations should be tested for effects on viability before attempting fusion. The molecular weight range of PEG may be varied from 1000 to 6000. It gives best results when diluted to from about 20% to about 70% (w/w) in saline or serum-free medium. Exposure to PEG at 37° C. for about 30 seconds is preferred in the present case, utilizing murine cells. Extremes of temperature (i.e., about 45° C.) are avoided, and preincubation of each component of the fusion system at 37° C. prior to fusion can be useful. The ratio between lymphocytes and malignant cells is optimized to avoid cell fusion among spleen cells and a range of from about 1:1 to about 1:10 is commonly used.

The successfully fused cells can be separated from the myeloma line by any technique known by the art. The most common and preferred method is to choose a malignant line which is Hypoxthanine Guanine Phosphoribosyl Transferase (HGPRT) deficient, which will not grow in an aminopterin-containing medium used to allow only growth of hybrids and which is generally composed of hypoxthanine $1 \times 10^{-4}$ M, aminopterin $1 \times 10^{-5}$ M, and thymidine $3 \times 10^{-5}$ M, commonly known as the HAT medium. The fusion mixture can be grown in the HAT-containing culture medium immediately after the fusion 24 hours later. The feeding schedules usually entail maintenance in HAT medium for two weeks and then feeding with either regular culture medium or hypoxthanine, thymidine-containing medium.

The growing colonies are then tested for the presence of antibodies that recognize the antigenic preparation. Detection of hybridoma antibodies can be performed using an assay where the antigen is bound to a solid support and allowed to react to hybridoma supernatants containing putative antibodies. The presence of antibodies may be detected by "sandwich" techniques using a variety of indicators. Most of the common methods are sufficiently sensitive for use in the range of antibody concentrations secreted during hybrid growth.

Cloning of hybrids can be carried out after 21–23 days of cell growth in selected medium. Cloning can be preformed by cell limiting dilution in fluid phase or by directly selecting single cells growing in semi-solid agarose. For limiting dilution, cell suspensions are diluted serially to yield a statistical probability of having only one cell per well. For the agarose technique, hybrids are seeded in a semi-solid upper layer, over a lower layer containing feeder cells. The colonies from the upper layer may be picked up and eventually transferred to wells.

Antibody-secreting hybrids can be grown in various tissue culture flasks, yielding supernatants with variable concentrations of antibodies. In order to obtain higher concentrations, hybrids may be transferred into animals to obtain inflammatory ascites. Antibody-containing ascites can be harvested 8–12 days after intraperitoneal injection. The ascites contain a higher concentration of antibodies but include both monoclonals and immunoglobulins from the inflammatory ascites. Antibody purification may then be achieved by, for example, affinity chromatography.

Example 15

Detection of Antibodies

The present invention contemplates the detection of antibodies to ferritin binding protein in the brain. In one embodiment antibodies will be detected via an indirect immunofluorescence test for detection of IgG antibodies to ferritin binding proteins in the brain. Antigen slides of substantially purified ferritin binding protein in the brain will be incubated with serum samples screened at serial dilutions. In one embodiment, an isothiocyanate fluorescein labeled rabbit IgG anti-goat IgG will be used as secondary antibody. Positive control sera may be obtained from animals with consistently positive serological results. Negative control sera will be obtained from animals with consistently negative serological. The slides may be examined by epi-fluorescent microscope.

In another embodiment an immunoenzymatic test (ELISA) will be carried out for detection of IgG antibodies ferritin binding proteins in the brain. Microtiter plates will be coated overnight at 4° C. with a soluble antigen preparation (0.25 mg of protein/well), consisting of a sonicated extract of substantially pure ferritin binding protein diluted in 0.06M sodium carbonate buffer (pH 9.6). The plates will be washed three times with phosphate-buffered saline containing 0.05% Tween 20 (PBST) and incubated with the samples. Dilutions of serum samples from patients suspected of having MS will be added in duplicates to the plate wells and the plates incubated at 37° C. for 45 min. After repeated washing, the secondary antibody, consisting of a peroxidase (horseradish peroxidase, type VI, Sigma Co., St. Louis, USA) labeled to rabbit IgG anti-dog IgG and diluted 1:20,000 in PBST/ES, will added and incubation performed for 45 min at 37° C. After a final wash, the plates will be incubated with enzyme substrate hydrogen peroxide and o-phenylenediamine (Merck, Germany) in 0.1M citrate-$Na_2HPO_4$ buffer (pH 5.5) for 15 min at room temperature. The reaction will be stopped by adding 2N $H_2SO_4$ and the absorbance will read at 492 nm. Positive and negative serum controls previously tested by conventional serological tests will be included on each plate. Samples showing absorbance values exceeding the mean absorbance of the negative controls plus 2 standard deviations will be considered as positive.

Accordingly, this invention is not limited to the particular embodiments disclosed, but is intended to cover all modifications that are within the spirit and scope of the invention as defined by the appended claims

We claim:

1. A method for the detection of multiple sclerosis comprising:
    a) providing:
        i) a brain tissue sample, having a periplaque region, from a human suspected of having a demyelinating disease and
        ii) transferrin;
    b) reacting, in vitro, said brain tissue sample with transferrin; and
    c) evaluating said periplaque region for binding with transferrin wherein a finding of transferrin binding, in said periplaque region, confirms the detection of multiple sclerosis in said brain tissue sample.

* * * * *